United States Patent
Zografos et al.

(10) Patent No.: US 11,692,988 B2
(45) Date of Patent: *Jul. 4, 2023

(54) DNA BASED BAR CODE FOR IMPROVED FOOD TRACEABILITY

(71) Applicants: SafeTraces, Inc., Oakland, CA (US); Lawrence Livermore National Security, LLC, Livermore, CA (US)

(72) Inventors: Antonios Zografos, Oakland, CA (US); George Roy Farquar, Livermore, CA (US)

(73) Assignees: SafeTraces, Inc., Oakland, CA (US); Lawrence Livermore National Security, LLC, Livermore, CA (US)

( * ) Notice: Subject to any disclaimer, the term of this patent is extended or adjusted under 35 U.S.C. 154(b) by 906 days.

This patent is subject to a terminal disclaimer.

(21) Appl. No.: 16/386,147

(22) Filed: Apr. 16, 2019

(65) Prior Publication Data

US 2019/0285602 A1     Sep. 19, 2019

Related U.S. Application Data

(63) Continuation of application No. 14/599,315, filed on Jan. 16, 2015, now Pat. No. 10,302,614.

(Continued)

(51) Int. Cl.
*G01N 33/02* (2006.01)
*C12N 15/10* (2006.01)
(Continued)

(52) U.S. Cl.
CPC ............ *G01N 33/02* (2013.01); *A23L 29/045* (2016.08); *C07H 21/04* (2013.01);
(Continued)

(58) Field of Classification Search
CPC ... A23L 29/045; A23V 2002/00; C07H 21/04; C12N 15/1065; C12Q 1/6806; C12Q 1/686; C12Q 2563/185; G01N 33/02
See application file for complete search history.

(56) References Cited

U.S. PATENT DOCUMENTS

| | | |
|---|---|---|
| 1,913,069 A | 6/1933 | Chance |
| 4,593,360 A | 6/1986 | Cocks |

(Continued)

FOREIGN PATENT DOCUMENTS

| | | |
|---|---|---|
| CN | 101379188 A | 3/2009 |
| CN | 104024426 A | 9/2014 |

(Continued)

OTHER PUBLICATIONS

Andrews, "DNA Spray-On Technology Could Revolutionize Food Traceability," Food Safety News, http://www.foodsafetynews.com/2014/11/dna-laced-spray-technology-could-revolutionize-food-traceability/#.W1kRNNVKjRY, Nov. 17, 2014, 2 pages.

(Continued)

*Primary Examiner* — Jeremy C Flinders
(74) *Attorney, Agent, or Firm* — Haynes and Boone LLP (57) ABSTRACT

Food distributed to consumers through a distribution chain may be traced by tagging the food with DNA tags that identify the origin of the food, such as the grower, packer and other points of distribution, and their attributes. This makes it much quicker and easier to trace the food in case of food contamination or adulteration. Preferably these attributes indicate the field, location, crew and machine used to grow and process the food, and the dates of the various steps of food harvesting, processing and distribution. Natural or synthetic DNA pieces may be used to tag items, including food items. Multidigit binary or other types of bar codes may be represented by multiple types of DNA. Each digit of the bar code may be represented by one, two or more unique DNA pieces.

20 Claims, 4 Drawing Sheets

Related U.S. Application Data (60) Provisional application No. 62/053,859, filed on Sep. 23, 2014, provisional application No. 61/988,978, filed on May 6, 2014.

(51) Int. Cl.
| | | |
|---|---|---|
| *C07H 21/04* | (2006.01) | |
| *A23L 29/00* | (2016.01) | |
| *C12Q 1/6806* | (2018.01) | |
| *C12Q 1/686* | (2018.01) | |

(52) U.S. Cl.
CPC ....... *C12N 15/1065* (2013.01); *C12Q 1/6806* (2013.01); *C12Q 1/686* (2013.01); *A23V 2002/00* (2013.01); *C12Q 2563/185* (2013.01)

(56) References Cited

U.S. PATENT DOCUMENTS

| | | |
|---|---|---|
| 6,312,911 B1 | 11/2001 | Bancroft et al. |
| 8,293,535 B2 | 10/2012 | Farquar et al. |
| 2002/0129523 A1 | 9/2002 | Hunt |
| 2004/0166520 A1 | 8/2004 | Connolly |
| 2005/0031487 A1 | 2/2005 | Rosenblatt |
| 2006/0037222 A1 | 2/2006 | Hunt et al. |
| 2006/0111845 A1 | 5/2006 | Forbis et al. |
| 2009/0070134 A1 | 3/2009 | Rodgers |
| 2010/0159434 A1 | 6/2010 | Lampotang et al. |
| 2010/0261193 A1 | 10/2010 | Webster et al. |
| 2011/0165569 A1 | 7/2011 | Macula |
| 2011/0177539 A1 | 7/2011 | Sutton et al. |
| 2012/0112883 A1 | 5/2012 | Wallace et al. |
| 2013/0052751 A1 | 2/2013 | Farquar et al. |
| 2013/0122807 A1 | 5/2013 | Tenarvitz et al. |
| 2014/0046722 A1 | 2/2014 | Rosenbloom et al. |
| 2014/0057276 A1 | 2/2014 | Farquar et al. |
| 2014/0108039 A1 | 4/2014 | Rensvold et al. |
| 2014/0220576 A1 | 8/2014 | Macula |
| 2014/0255984 A1 | 9/2014 | Sharpin |
| 2014/0272097 A1 | 9/2014 | Jung et al. |
| 2014/0340423 A1 | 11/2014 | Taylor et al. |
| 2015/0361490 A1 | 12/2015 | Farquar et al. |
| 2016/0102335 A1 | 4/2016 | Franciskovich et al. |
| 2016/0171179 A1 | 6/2016 | Donofrio et al. |
| 2016/0188943 A1 | 6/2016 | Franz |
| 2017/0197002 A1 | 7/2017 | Dobrinsky et al. |
| 2017/0322701 A1 | 11/2017 | Bowman et al. |
| 2017/0333859 A1 | 11/2017 | Lind |
| 2018/0252738 A1 | 9/2018 | Denney |

FOREIGN PATENT DOCUMENTS

| | | |
|---|---|---|
| CN | 104131008 A | 11/2014 |
| CN | 104513863 A | 4/2015 |
| WO | 2008137831 A1 | 11/2008 |
| WO | 2011163296 A2 | 12/2011 |
| WO | 2012037876 A1 | 3/2012 |
| WO | 2014164958 A1 | 10/2014 |

OTHER PUBLICATIONS

Busta et al., "The Use of Indicators and Surrogate Microorganisms for the Evaluation of Pathogens in Fresh and Fresh-Cut Produce," Comprehensive Reviews in Food Science and Food Safety, 2(s1), Jan. 2003, pp. 179-185.

Bystrykh, "Generalized DNA Barcode Design Based on Hamming Codes," PLOS One 7(5):e36852, May 17, 2012, 8 pages.

Danyluk et al., "Process Validation: Selection and Use of Surrogates," University of Florida Institute of Food and Argicultural Sciences, presentation dated Apr. 2014, 19 pages.

Extended European Search Report dated Feb. 26, 2019, European Patent Application No. 16833458.9, filed Jun. 17, 2016, 5 pages.

Farquar, "DNATrax (DNA Tagged Reagents for Aerosol eXperiments)," Lawrence Livermore National Laboratory, presentation LLNL-PRES-642415, Aug. 2013, retrieved from the internet at <http://web.archive.org/web/20160226230017/https://ipo.llnl.gov/technologies/individual-tech-discovery&p=DNATrax;, 6 pages.

Harding et al., "Unique DNA-barcoded aerosol test particles for studying aerosol transport," Aerosol Science and Technology 50(5):429-435, Mar. 22, 2016.

Hou et al., "Rapid bioparticle concentration and detection by combining a discharge driven vortex with surface enhanced Raman scattering," Biomicrofluids 1.014106:1-13, Feb. 16, 2007.

International Search Report and Written Opinion dated Aug. 8, 2019, International Patent Application No. PCT/US2019/029002, filed Apr. 24, 2019, 8 pages.

International Search Report and Written Opinion dated Sep. 8, 2016, International Patent Application No. PCT/US2016/038083, filed Jun. 17, 2016.

International Search Report and Written Opinion, dated Mar. 15, 2019, International Patent Applicaton No. PCT/US19/13069, filed Jan. 10, 2019, 13 pages.

Ma et al., "Development of Thermal Surrogate Microorganisms in Ground Beef for In-Plant Critical Control Point Validation Studies," Journal of Food Protection, 70(4), Apr. 2007, pp. 952-957.

Naaum, "Novel Methods of Species and Product Authenticity and Traceability Testing Using DNA Analysis for Food and Agricultural Applications," Doctoral Dissertation, Department of Integrative Biology University of Guelph, Apr. 2014, 144 pages.

Niebuhr et al., "Evaluation of non-pathogenic surrogate bacteria as process validation indicators for *Salmonella enteric* for selected antimicrobial treatments, cold storage and fermentation in meat," Journal of Food Protection, 71(4), Apr. 2008, pp. 714-718.

Oxford Gene Technology, "DNA Storage and Quality," Aug. 2011 [retrieved Oct. 30, 2018 https://www.ogt.com/resources/literature/403_dna_storage_and_quality, 5 pages.

Puddu et al., "Magnetically Recoverable, Thermostable, Hydrophobic DNA/Silica Encapsulates and Their Application as Invisible Oil Tags," ACS Nano 8(3):2677-2685, Feb. 25, 2014.

Sharma et al., "Hydrological Tracers Using Nanobiotechnology: Proof of Concept," Environmental Science and Technology, 46(16):8928-8936, Aug. 21, 2012.

Sinclair et al., "A Criteria for Selection of Surrogates Used to Study the Fate and Control of Pathogens in the Environment," Applied and Environmental Microbiology, 78(6), published online Jan. 13, 2012, published in print Mar. 2012, pp. 1969-1977.

Yeater et al., "Effectiveness of Sanitzing Products on Controlling Selected Pathogen Surrogates on Retail Deli Slicers," Journal of Food Protection, 78(4), Apr. 2015, pp. 707-715.

Ruther, "Assistive Systems for Quality Assurance by Context-aware User Interfaces in Health Care and Production," Diss. Universitatsbibliotiek Bieiefeld (2014).

Galimberti et al., 'DNA barcoding for minor crops and food traceability' Advances in Agriculture, vol. 2014, Article ID.831875, internal pp. 1-8 (2014).

Galimberti et al., 'DNA barcoding as a new tool for food traceability' Food Research International, vol. 50, Issue.I, pp. 55-63 (2013).

International Search Report and Written Opinion dated Aug. 12, 2015, International Patent Application No. PCT/US2015/028880.

| | 1 | 0 | 1 | 0 | 0 | 0 | 0 | 1 |
|---|---|---|---|---|---|---|---|---|
| Bit=1 | ATCAA | ATCAG | ATCCA | ATCGA | ATAAA | ATTAA | ATGAA | AAGAA |
| Bit=0 | ATCAC | ATCTA | ATGAA | ACGAA | TCGAA | CCGAA | GCGAA | AGCTA |
| Bit=1 | APPLE | PEAR | KIWI | PLUM | ORANGE | KALE | GUAVA | CARROT |
| Bit=0 | BEET | POTATO | ONION | BEAN | LEEK | MANGO | WALNUT | PEACH |

FIG. 4

DNA BASED BAR CODE FOR IMPROVED FOOD TRACEABILITY

CROSS-REFERENCES TO PRIORITY AND RELATED APPLICATIONS

This application claims priority from and is a continuation of U.S. Non-Provisional application Ser. No. 14/599,315, filed on Jan. 16, 2015, entitled "DNA Based Bar Code for Improved Food Traceability," which claims the benefit of U.S. Provisional Patent Application No. 62/053,859, filed Sep. 23, 2014, entitled "Method to represent binary numbers using DNA," and U.S. Provisional Patent Application No. 61/988,978, filed May 6, 2014, entitled "Use of DNATrax or other tagged DNA based barcode for improved food traceability."

BACKGROUND

We live in a world of globalization, a world in which political and commercial realities are the drivers for increasing supply chain efficiencies, accountability and security. One key to achieving gains in all three areas lies in the area of traceability. For the global food industry, supply chain traceability is, today, more than ever, a high visibility issue. Traceability is the ability to trace the history, application or location. Whole-chain food traceability is comprised of both "tracking" and "tracing". "Tracking" is the ability to follow the path of a traceable item through the supply chain as it moves between parties. "Tracing" is the ability to identify the origin, attributes, or history of a particular traceable item located within the supply chain by reference to records held.

Food traceability is becoming increasing important. The global food supply chain today has evolved into a tangled web. The pathway from primary production to the consumer is growing more complex as companies seek higher efficiencies to feed the world's growing population. While problems remain rare, when they do occur, time is the enemy as current traceability systems struggle to respond. Health and lives are at stake, as well as the livelihoods of industries, companies, and employees.

In the USA the 3,000 deaths that foodborne illness causes each year, is very expensive. The cost of food poisoning comes to $14 billion a year, according to a July 2012 study published in the Journal of Food Protection, including the medical expenses of the 128,000 who are hospitalized annually. That figure does not include the millions of dollars that each food recall costs a company involved, the legal expenses from victims' lawsuits or losses incurred by other companies when consumers hear, for example, about contaminated produce and then avoid that entire commodity, including that which is perfectly safe. Government regulators are increasingly concerned about the time taken to respond to food-related emergencies, as consumer trust in food becomes more fragile.

However, food traceability is about more than recalls. Food fraud is becoming a very important issue. It is estimated that food fraud costs the global food industry over $15 billion annually and the cost is rapidly rising. Being able to ascertain the origin of products and their attributes from the farm through food processing, to retail and food service, and into the home is growing in importance. Increasingly, public health concerns are demanding traceability. But economic advantage, which rewards those who can more effectively and reliably track and trace product back and forth through each step of the chain, will eventually drive traceability.

Improved food traceability will benefit: (a) the FDA by reducing the resources required to complete an investigation; (b) public health since reduction of the duration of investigation of food related illnesses is key to the containment of an outbreak, and; (c) the industry, by facilitating the ability to isolate the source and extent of safety and/or quality control issues and minimizing the scope of product to be recalled and the time to execute a recall as well as all associated liabilities.

Food traceability today entails a complex system of hand offs along the supply chain from producer to packer, distributor, retailer and ultimately the consumer. Product identification is applied most often to the packaging. In most instances when a consumer detects product contamination or symptoms of illness, it may be days or weeks after the purchase date. Packaging (shrink wrap, bags, etc.) or product identification may not exist or have been discarded. Given the time elapsed, the product implicated may well have completed its cycle through the supply chain.

It is therefore desirable to provide an improved system and method for tracing food products throughout the supply chain.

SUMMARY

One embodiment is directed to a food product made and distributed to consumers along multiple nodes of a distribution chain. The food product comprises a food material; and at least one DNA bar code attached to or mixed with the food material, the at least one DNA bar code identifying at least two attributes of at least one node of the distribution chain.

Another embodiment is directed to a food product, comprising a first food material and a second material including at least one DNA bar code for identifying an attribute of the food material, the second material mixed with the food material. The attribute identifies a predetermined value of a proportion between the food material and the second material.

Yet one more embodiment is directed to a food product, comprising a first food material; and a second material including at least one DNA bar code for identifying an origin of the food material, the second material being bound to the first material, so that mixing the first food material with other materials will not cause the second material to be bound to the other materials.

Still another embodiment is directed to an agglomeration of a first food material and a second material including at least one DNA bar code for identifying an origin of the food material.

An additional embodiment is directed to an agglomeration of a first food material and a second material including at least one DNA bar code indicating a predetermined value of an attribute that indicates purity or concentration of the food material.

One more embodiment is directed to a method for applying to a food material a second material for identifying the food material, comprising mixing said second material with or applying said second material to said food material, said second material including at least one DNA bar code for identifying an origin of the food material.

Yet one more embodiment is directed to a method for tracing the origin of a food material, wherein the food material has been labeled by a second material that includes tags of at least one DNA bar code for identifying at least one origin of the food material. The method comprises causing polymerase chain reaction of the second material through one or more heating cycles to increase number of copies of a specific target fragment of the DNA bar code; detecting the copies of the specific target fragment of the DNA bar code in the second material; and analyzing tags of the detected specific target fragment to identify the at least one origin of the food material.

Still another embodiment is directed to a product comprising an item and a material for tagging the item, the material including at least N unique pieces of DNA, representing N digits of a bar code that identifies an attribute of the item. Each of the at least N pieces of DNA represents one value of a corresponding one of the N digits, N being a positive integer greater than 1.

Yet another embodiment is directed to a method for identifying an attribute of an item, comprising providing a material for tagging the item, the material including at least N unique pieces of DNA, representing N digits of a bar code that identifies an attribute of the item, N being a positive integer greater than 1, wherein each of the at least N pieces of DNA represents one value of a corresponding one of the N digits, and wherein detection of the attribute does not permit the item to be authenticated or identified. The material is used to tag the item.

One more embodiment is directed to a method for detecting an attribute of an item tagged by a material, the material including at least N unique pieces of DNA, representing N digits of a bar code that identifies the attribute of the item, N being a positive integer greater than 1, wherein each of the at least N pieces of DNA represents one value of a corresponding one of the N digits. The method includes detecting pieces of DNA tagged to the item; deriving a bar code from the detected pieces of DNA; and comparing the derived bar code to a predetermined bar code that identifies the attribute to detect the attribute, wherein detection of the attribute does not permit the item to be authenticated or identified.

All patents, patent applications, articles, books, specifications, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

DETAILED DESCRIPTION OF EXEMPLARY EMBODIMENTS

Advances in biology have produced materials that enable the development of a very efficient, effective and low cost food tracing system. One such material is DNATrax. DNATrax has been used as simulants of bio-threat microparticles for simulating terrorist attacks, and for tracking and quantifying particulate migration. See for example, U.S. Pat. No. 8,293,535 and U.S. Application 2014/0057276. U.S. Application 2014/0272097 discloses DNA marking of items for authenticating the items. However, none of the above documents relates to the problem of tracing items to the origin of these items, such as the problem of tracing the origin of food products.

DNATrax offers an opportunity to trace food along multiple steps in the supply chain and ultimately to the consumer by applying the product identification directly on many food products, at a cost significantly lower than any other method. DNATrax is a safe and versatile material containing food-based FDA-approved sugars, and a unique non-biological DNA tag. DNATrax is described in an article entitled "DNA Tagged Reagents for Aerosol Experiments (DNATrax)." The resulting microparticle can be sprayed directly onto the product or mixed with a coating and will adhere to produce and other food surfaces. A practically limitless number of tags are possible by using synthetic DNA. Naturally occurring DNA may also be used as described below.

Food is prepared from a living thing that is typically first grown (e.g. fruits and vegetables) or raised (e.g. land animals or sea creatures). For simplicity in description, a grower herein includes entities that grow living things and entities that raise living things. The living things are then packaged by packers. In the case of land animals or sea creatures (also referred to as "food" hereinbelow), they are first slaughtered before being packaged. Then the packaged food is distributed through various distribution outlets to the consumer, such as through neighborhood stores and supermarkets, or restaurants, caterers and food courts. The distribution chain of the food product thus includes the grower, the packer, and the distribution outlets, where each of the points where food is handled in the distribution chain constitutes a node in the distribution chain. Contamination and tempering can thus occur at any one or more of the nodes in the distribution chain. One embodiment of the invention is based on the recognition that, by providing the food launched in the distribution chain with a material that identifies two or more of the attributes of one or more of the nodes in the distribution chain, it becomes much easier and efficient to accurately trace the possible source of food contamination and tempering.

Figure 1:
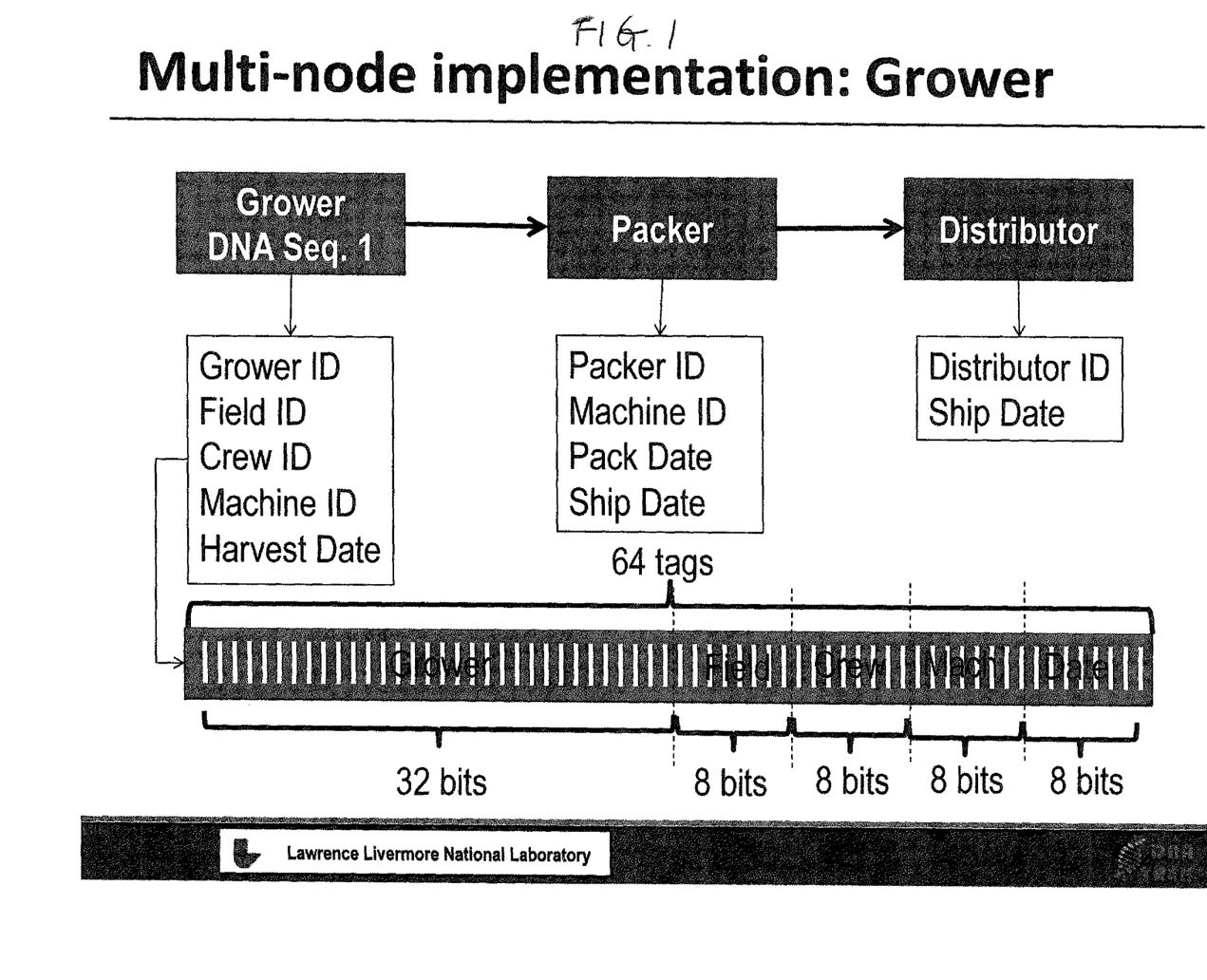
FIG. 1 is a flow chart illustrating a distribution chain of a food product to illustrate one embodiment of the invention, where the food product has been labeled with a DNA bar code with 64 tags for identifying a grower of the food product.

FIG. 1 is a flow chart illustrating a distribution chain of a food product to illustrate one embodiment of the invention, where the food product has been labeled with a DNA bar code with 64 bits for identifying a grower of the food product. As shown in FIG. 1, the food product originates at the grower, who ships the food to the packer who in turn ships the food product to the distributor. The 64 bits of the DNA bar code or tag ("bar code" and "tag" are used interchangeably herein) are used for identifying two or more attributes related to the grower. In this particular implementation shown in FIG. 1 of the embodiment, the 64 bits are divided into 5 groups that identify 5 grower attributes, with 32 bits used for identifying the grower, 8 bits for identifying the field or location where the food was grown or raised, another 8 bits for identifying the crew that was involved in growing and harvesting the food or raising the food, another 8 bits for identifying one or more machines (e.g. used for harvesting or slaughtering) that processed the food after it had been grown or raised, and yet another 8 bits to identify the date or dates on which the food was grown (e.g. harvest date) or raised and processed (e.g. date of slaughter). Different growers will have different grower ID tags, and the same is true for different fields, crews, machines and harvest dates for the same grower. To make it possible to trace the origin of a food product that has been tagged by a DNA bar code with 64 bits such as that shown in FIG. 1, the ID tags of all of the growers who have tagged their food products are stored in a database (not shown) as well as the ID tags of their fields, crews, machines and harvest dates, as predetermined bar codes. Then when it is necessary to trace the origin of a particular food product that has been so tagged, the DNA tags of such product can be compared to the predetermined bar codes in the database to determine its origin as far as the grower is concerned.

While including all 5 grower attributes as shown in FIG. I is desirable, for some applications, including only two or three or four attributes may be useful and adequate. For example, the machine or location ID may be omitted so that the DNA bar code identifies only 4 of the 5 attributes shown in FIG. 1. Where both the machine and location IDs are omitted, then the DNA bar code identifies only 3 of the 5 attributes. Obviously, a different number of bits than those shown in FIG. 1 may be allocated for identifying any one or more of the attributes, and obviously the bits may be used for identifying grower attributes that are different from those shown in FIG. 1. Such and other variations are within the scope of the invention.

Figure 2:
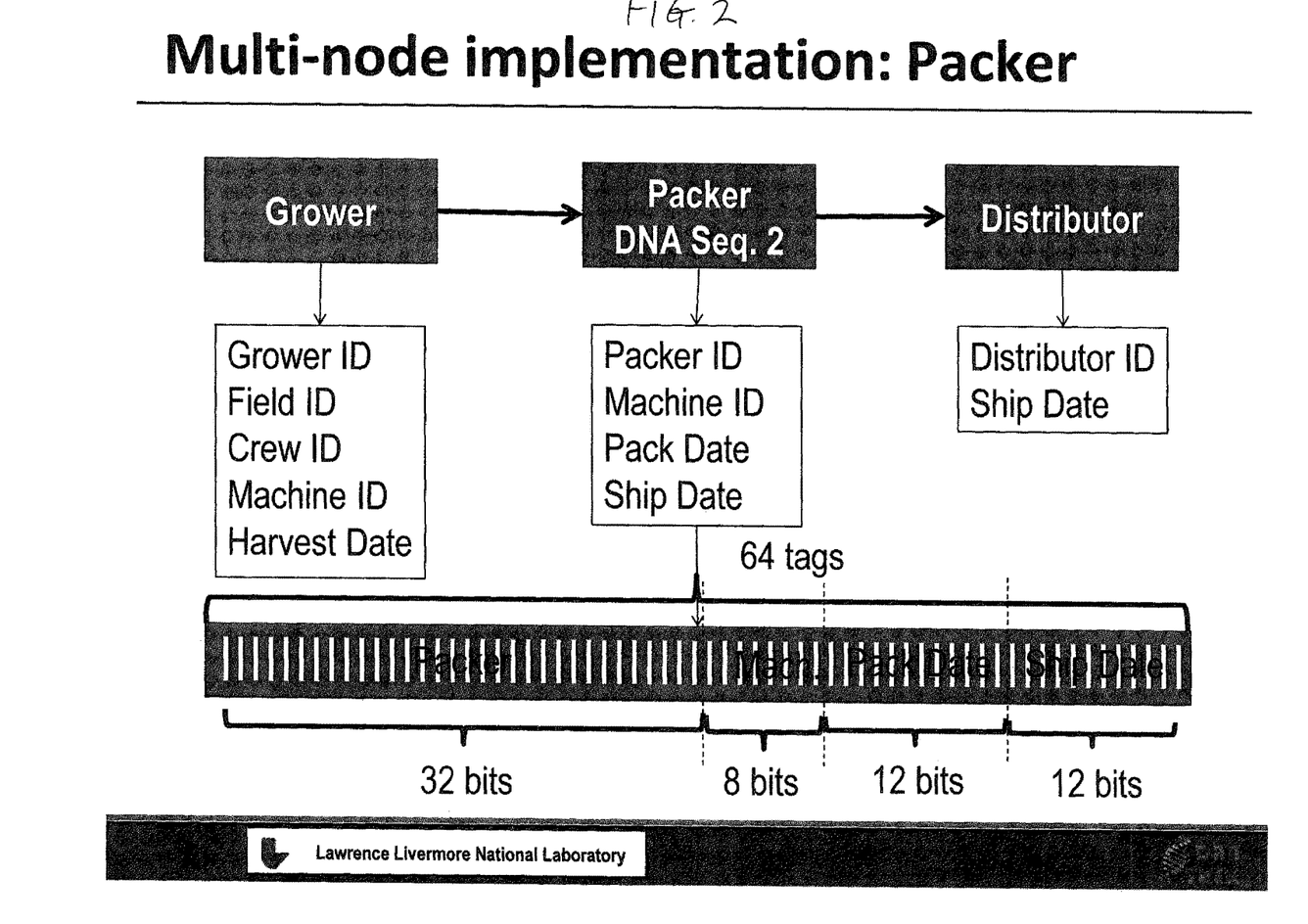
FIG. 2 is a flow chart illustrating a distribution chain of a food product to illustrate another embodiment of the invention, where the food product has been labeled with a DNA bar code with 64 tags for identifying a packer of the food product.

FIG. 2 is a flow chart illustrating a distribution chain of a food product to illustrate another embodiment of the invention, where the food product has been labeled with a DNA bar code with 64 bits for identifying a packer of the food product. As shown in FIG. 2, the food product originates at the grower, who ships the food to the packer who in turn ships the food product to the distributor. The 64 bits of the DNA bar code are used for identifying two or more attributes related to the packer. In this particular implementation shown in FIG. 2 of the embodiment, the 64 bits are divided into 4 groups that identifies 4 packer attributes, with 32 bits used for identifying the packer, 8 bits for identifying the one or more machines that packaged the food after it had been processed by the grower and shipped to the packer, 12 bits to identify the date or dates on which the food was packed (e.g. package date), and another 12 bits for identifying the shipment date of the packed food to the food distribution outlets. Thus the DNA sequences that comprise the packer bar code are different from the DNA sequences that comprise the grower bar code and the two bar codes can be "read" independently of each other. As in the case of the grower, the ID tags of all of the packers who have tagged their food products are stored in a database (not shown) as well as the ID tags of their machines, packing and shipment dates. Then when it is necessary to trace the origin of a particular food product that has been so tagged, the DNA tag of such product can be compared to those in the database to determine its origin as far as the packer is concerned.

While including all 4 packer attributes as shown in FIG. 2 is desirable, for some applications, including only two or three attributes may be useful and adequate. For example, the machine ID or pack date may be omitted so that the DNA bar code identifies only 3 of the 4 attributes shown in FIG. 2. Where both the machine ID and pack date are omitted, then the DNA bar code identifies only 2 of the 4 attributes. Obviously, a different number of bits than those shown in FIG. 2 may be allocated for identifying any one or more of the attributes, and obviously the bits may be used for identifying grower attributes that are different from those shown in FIG. 2. Such and other variations are within the scope of the invention.

Providing the food launched in the distribution chain with a material that identifies two or more of the attributes of one or more of the nodes in the distribution chain is particularly advantageous for tracing the origin of food contamination and tempering. For example, a DNA bar code that provides information regarding not only the grower identity, but also the harvest or slaughter date will make it possible to determine if the food product produced by this grower has gone bad because there was a delay in delivering the harvested or slaughtered product to the packer. Similarly, a DNA bar code that provides information regarding not only the grower identity, but also the crew, machine or field identity will make it possible to determine if the food product produced by this grower has gone bad because of contamination or tempering by the crew, by the machine used to process the product or events at the location of the field or processing plant at which the contamination or tempering occurred, or a combination of the above. The same can be said for the DNA bar codes used for identifying two or more attributes related to the packer.

Since it is important to be able to trace the origin of the food contamination and tempering at each of the nodes of the distribution chain, it may be desirable to apply a material that contains DNA bar codes or tags for identifying the attributes of both the grower and packer. In addition to identifying the grower and packer, additional DNA bar codes or tags may be used for identifying one or more of the nodes of the distributions outlets to the consumer, such as for identifying two or more of the attributes (e.g. date of receipt of the food product) of neighborhood stores, supermarkets, restaurants, caterers or food courts. The DNA bits of these tags may be used to identify at least two attributes of one or more of the nodes of the distribution outlets. Ideally, the food product is tagged with DNA tags that identify the attributes of each one of these nodes in the distribution chain. This will enable the source of food contamination and tempering to be easily, quickly and efficiently traced to any one or more of the nodes of the distribution chain. The ID tags representing the different attributes of each one of the nodes in the distribution outlets to the consumer may be stored in a database, which is used for tracing the origin of food products in the same manner as described above for the grower and packer.

The detection can be multiplexed with both polymerase chain reaction ("PCR") detection and amplicon length variation. Variation of the amplicon length is possible due to the synthetic nature of the DNA. A natural sample would have a fixed length for each primer and probe set. The detection methods would allow source tracing in minutes as opposed to days or weeks.

Application of DNATrax on food products will be simple and will not require significant incremental capital investment. There already exist process steps in the supply chain of many produce and other food items where DNATrax can be safely added as a component. As examples:

DNATrax can be added as a component of Carnauba wax coatings. Carnauba wax is an edible coating frequently applied as an emulsion to produce such as:

Citrus Fruits: grapefruits, lemons, limes, oranges, tangerines

Melons: cantaloupe, honeydew

Pome Fruits: apples, pears

Stone Fruits: nectarines, peaches, plums

Tropical Fruits: mangos, papayas, passion fruit

Vegetables: avocados, bell peppers, cucumbers, eggplant, green peppers, hot peppers, parsnips, rutabaga, sweet potatoes, squash, tomatoes, and turnips.

It should be noted that for traceability purposes, it is not necessary to apply a full coating on the produce. Only a trace amount would suffice. Carnauba wax will prevent DNATrax from migrating to adjacent fruit not tagged with DNATrax in the event of commingling of produce from different origins. More generally, by binding the DNATrax to the food product (such as by means of a coating), mixing such food product with other food products not so tagged or labeled will not cause the other food products to become so tagged or labeled. The DNATrax may identify the origin of the food product, such as the identity of the grower, or packer, or two or more attributes of any one or more nodes in the distribution chain as described above. The food product may be tagged or labeled by mixing with the food product or applying to the food product identifying material or carrier that includes at least one DNA bar code for identifying the origin of the food product, such as the identity of the grower, and/or packer, or two or more attributes of any one or more nodes in the distribution chain as described above. The applying may include spraying the identifying material onto the food product.

- DNATrax may be added as a component to food grade silicone oil, which is frequently used as a coating for tropical fruit such a pineapple, mango, papaya, etc.
- DNATrax may be added as a component to sprout inhibitors used with potatoes.
- DNATrax may be added as a component to Vitamin C preparations used as a coating for cut fruit such as apples, pears, etc.
- DNATrax may be combined with lipid-, polysaccharide-, and protein-based edible coatings, as well as multicomponent edible coating systems, on meats, poultry, and seafood.
- DNATrax may be encapsulated in sugar, salt, starch or other material and added to and mixed with dry foods such as cereals, beans, and other dried foods to form an agglomeration.

Various other derivative methods may be developed to ensure stability of the DNA bar code on the food surface, maintain traceability through process steps such as heating, cooling, freezing drying, etc. In certain cases DNATrax may be applied on the produce in the field.

This method is not specific to DNATrax or a particular coating. Instead it relates to the use of bar coded DNA as an additive in any step of the food supply chain or process to establish traceability of the food item.

Some food products are in the form of individual pieces such as grain or of a liquid, such as olive oil, which is a liquid at room temperature. One possible way to temper with such products is to mix the grain or oil with another ingredient to dilute the product. Olive oil may be adulterated with olive oil from a different source or lower grade, other oils, etc. In the case of olive oil, DNATrax may be sprayed on the olive fruit before milling and will transfer to the oil during the milling process. Alternatively, DNATrax may also be diluted in olive oil and added to the product that needs to be tagged. The amount of DNATrax that would be needed to adequately "tag" olive oil would be in the range of 1 part per million or less. The amount of the DNATrax added to the grain or oil is controlled so that it bears a known ratio or proportion to the amount of food material that is mixed with the amount of the DNATrax added. This proportion is then used to determine the correct purity or concentration of the food material that has been so tagged. If the tagged food material is tempered with or adulterated by adding another substance to it, this will change the proportion between the added amount of DNATrax on one hand and the amount of original food material plus the amount of the substance added during the tempering on the other. This proportion can then be used to detect tempering and adulteration of the food material. The DNA bar code may then indicate the correct value of the proportion. Thus in another embodiment of the invention, the DNA bar code is attached to an identifying material that is mixed with the grain or oil, where the bar code identifies the correct proportion between the grain or oil and the identifying material. If the proportion between the grain or oil and the identifying material is different from that indicated by the DNA bar code, then this means that the food product has been tempered with. Thus in this embodiment, the attribute identified by the DNA bar code is the purity or concentration of the food product.

Where the food products are in the form of individual pieces, the identifying material may also be in the form of individual pieces, and a mixture of the food product with the identifying material will form an agglomeration. In another embodiment, the attribute identified by the DNA bar code on the identifying material in the agglomeration is the origin of the food products.

Figure 3A:
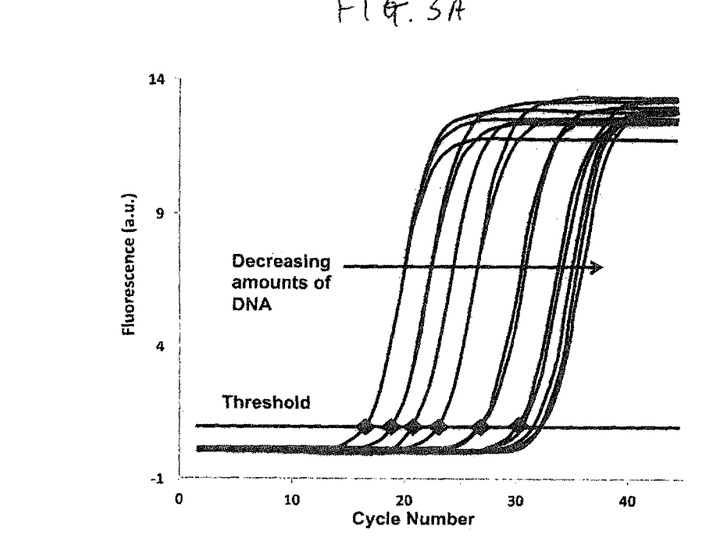
FIG. 3A is a graphical plot of fluorescence versus cycle number of a polymerase chain reaction useful for illustrating an embodiment of the invention.
Figure 3B:
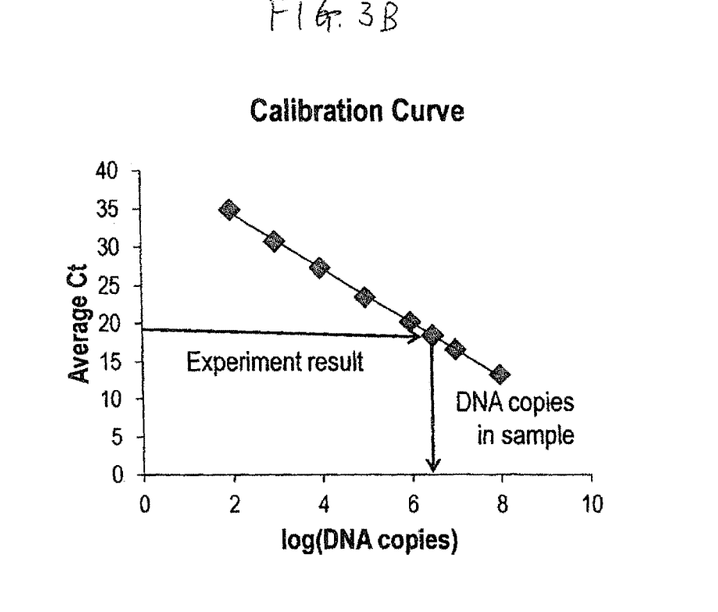
FIG. 3B is a graphical plot of a calibration curve of average cycle versus the logarithm of the number of DNA copies resulting from a polymerase chain reaction useful for illustrating an embodiment of the invention.

FIG. 3A is a graphical plot of fluorescence versus cycle number of a polymerase chain reaction ("PCR") useful for illustrating an embodiment of the invention. As known to those skilled in the art, a polymerase chain reaction includes heating a material that contains DNA pieces or segments ("DNA pieces" and "DNA segments" are used interchangeably herein) so that the DNA pieces undergo polymerase chain reactions that produce a large number of copies of the DNA pieces. In this manner, even trace amounts of the DNA can be readily detected. To measure the number of copies of the DNA pieces present, the DNA pieces are tagged with a fluorescent material, and the amount of fluorescence detected indicates the number of copies of the DNA pieces present. This is illustrated in FIG. 3A which shows the result detected from a number of samples with different number of copies of the DNA pieces. As illustrated in FIG. 3A, the smaller number of copies of the DNA pieces that are present initially before undergoing the heating cycles, the larger number of heating cycles will be necessary to amplify the number of copies so that the fluorescence from these copies become detectable. Thus, the initial number of copies of the DNA pieces is inversely related to the number of cycles necessary to amplify the number so that the fluorescence from these copies become detectable. FIG. 3B is a graphical plot of a calibration curve of the average cycle number versus the logarithm of the number of DNA copies produced by a polymerase chain reaction useful for illustrating an embodiment of the invention. The calibration curve of FIG. 3B may be constructed in advance based on actual measurements of the fluorescence of known number of copies of the DNA pieces. After this curve is constructed, the number of copies of the DNA pieces present in an unknown sample may be determined by finding the average number of heating cycles the sample has undergone to produce the required level of fluorescence. In lieu of the above detection technique, modern "digital" PCR systems are capable of detecting number individual segments in the sample without requiring a comparison to a calibration curve such as the one in FIG. 3B.

In the manner above, the number of copies of the DNA pieces present in an agglomeration or mixture of the food product with a second material containing the DNA pieces used to tag the food product may be determined. From this number and the volume of the tagged food product (e.g. olive oil tagged with DNATrax) or weight of the tagged food product (e.g. mixture of dry foods such as cereals, beans with DNATrax encapsulated in sugar, salt, starch or other material), one can determine whether the food product has been adulterated, such as by mixing the product with another cheaper ingredient.

To identify the origin of a food material labeled by a second material containing DNA barcode, the food material is heated to undergo polymerase chain reactions to amplify the number of copies of the bar code. This bar code is then analyzed to identify the origin of the food material. In addition, the DNA bar code may also indicate the correct purity or concentration as described above. The number of copies of the DNA bar code may be detected by comparing the number of cycles needed to produce the expected level of fluorescence, and this number is compared to the calibration curve shown in FIG. 3B to determine whether the food material has been tempered with in the manner described above.

DNA BAR CODES

System and Method to Represent Binary Numbers with DNA

We describe a method for producing multi digit bar codes or binary number identifiers by using multiple types of DNA. Binary numbers are represented by digital ones and zeros. A combination of 16 ones and zeros in a row produces a 16 bit number with a total possibility of $2^{16}=65536$ unique combinations. We have developed a method to use DNA in place of the digital ones and zeros to represent a number.

Figure 4:
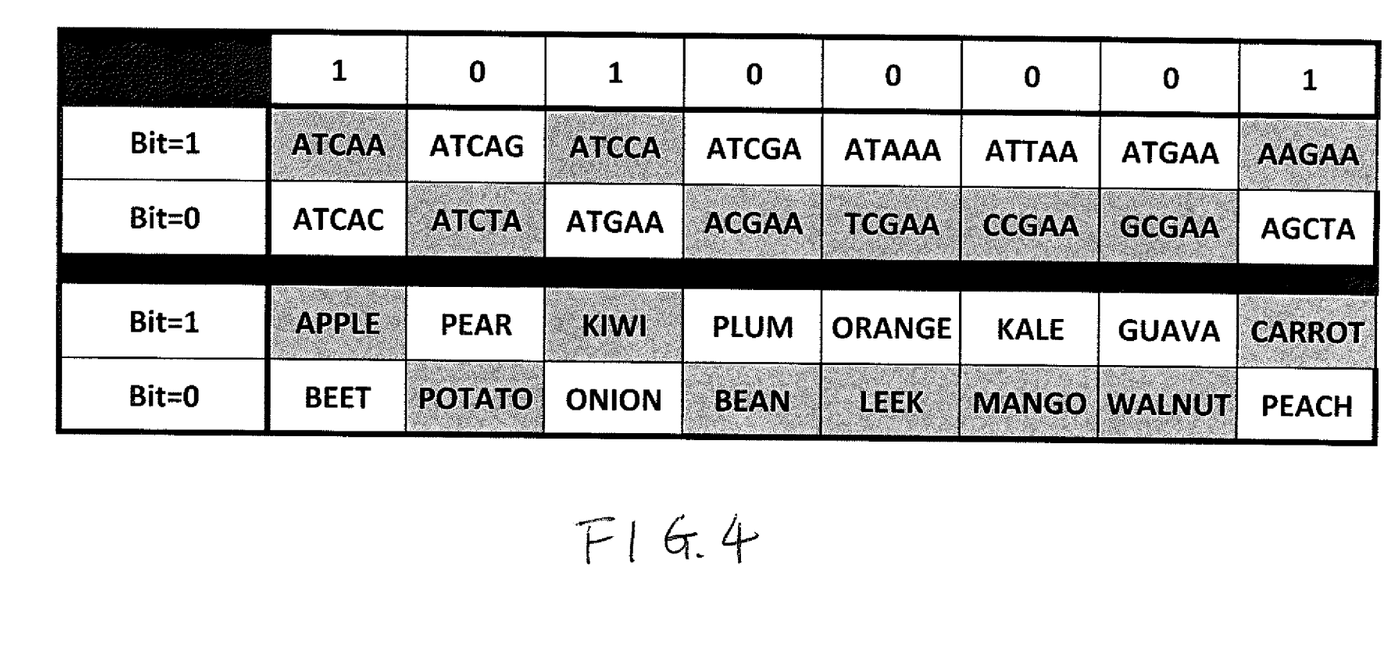
FIG. 4 is a schematic view of a table listing DNA pieces and fruit or vegetable DNA that uniquely identify binary numbers to illustrate another embodiment of the invention.

For example using 16 unique pieces of DNA we can represent a 16 bit number. Presence of a specific DNA piece indicates a "1" and absence indicates a "0". In certain applications it is advantageous to use two unique pieces of DNA for each bit so that 32 unique bits of DNA are used to represent a 16 bit number. For each bit there will be a unique piece of DNA representing "1" and a unique bit of DNA representing "0". This approach reduces the likelihood of false readings. Even in the event of cross contamination, the dominant piece of DNA will indicate the true status of the bit. This method increases the ability to use DNA tags for identification. Modern PCR detection and sequencing detectors can detect the individual presence of the bits and provide the digital equivalent of the DNA code that is present. An additional method can be envisioned where the DNA for each bit comes in more than one length. For example the DNA representing bit 0 in position 1 could be short, medium or long. This variation could increase the detection of number of possible bit DNA by a factor of 3. Yielding a possible set of combinations of 2.81475E+14, if 32 pieces of long medium and short DNA were used. The DNA length can be detected by a variety of common lab devices including sequencing and capillary electrophoresis FIG. 4 is a schematic view of a table listing DNA pieces (e.g. synthetic DNA as in DNA Trax) and fruit or vegetable DNA that uniquely identify binary numbers to illustrate the above described embodiment. Shown in the top row of FIG. 4 is an eight digit binary number "10100001." The second row lists the DNA segments for the value "1" of the eight digits, and the third row lists the DNA segments for the value "0" of the eight digits. It should be noted that the DNA segments in both the second and third rows are unique and different from one another. The DNA segments may also differentiate from one another by having different lengths instead of having different sequences as shown in FIG. 4. The top three rows of FIG. 4 illustrate one embodiment where the value "1" for the first digit is indicated by the presence of the DNA segment ATCAA, and the value "0" for the first digit is indicated by the presence of the DNA segment ATCAC. The value "1" for the second digit is indicated by the presence of the DNA segment ATCAG, and the value "0" for the first digit is indicated by the presence of the DNA segment ATCTA. Thus, the binary number "10100001" is represented by the presence of DNA segments ATCAA, ATCTA, ATCCA, ACGAA, TCGAA, CCGAA, GCGAA and AAGAA, and the absence of DNA segments ATCAC, ATCAG, ATGAA, ATCGA, ATAAA, ATTAA, ATGAA and AGCTA.

An alternative method to produce the binary numbers is envisioned where the DNA is taken from naturally occurring materials. The fourth row lists the natural DNA samples for the value "1" of the eight digits, and the fifth row lists the natural DNA samples for the value "0" of the eight digits. It should be noted that the DNA samples in both the fourth and fifth rows are unique and different from one another. For example digit 1 could consist of DNA from apple and beet, bit 2 pear and potato. By using extracted DNA and not synthetic, the material would be 100% natural and could meet specific requirements such as organic food, pesticide free, vegetarian, etc. The top row and the last two rows of FIG. 4 illustrate the embodiment using natural DNA. In this embodiment, the value "1" for the first digit is indicated by the presence of the apple DNA segment, and the value "0" for the first digit is indicated by the presence of the beet DNA segment. The value "1" for the second digit is indicated by the presence of the potato DNA segment, and the value "0" for the first digit is indicated by the presence of the pear DNA segment. Thus, the binary number "10100001" is represented by the presence of DNA segments of apple, potato, kiwi, bean, leek, mango, walnut and carrot, and the absence of DNA segments of beet, pear, onion, plum, orange, kale, guava and peach.

In other words, in FIG. 4, both the DNA fragment methods and the food DNA methods are demonstrated for an 8 bit binary number using 2 unique DNA pieces per bit. The top row of the figure represents a typical 8 bit binary number. The second and third lines represent unique DNA sequences that are assigned to be a 1 and 0 for each digit of the binary number. The darker boxes indicate what DNA samples would have to be present to represent each bit of the binary number "10100001". In the third and 4th rows as an example is shown where 16 food product DNA samples could be used to represent the 8 bit binary number "10100001". The samples needed to represent the number are shown in darker boxes.

In both embodiments each DNA segment or food sample is assigned a value 0 or 1 and a bit digit position. For example the kiwi is assigned to position 3 with the bit value 1. This unique location and value identification allows for the identification of the original number no matter what order the DNA is identified in. If KIWI is identified it can only be in position 3 to indicate a bit value 1.

Using the above system, a product may include an item and a material for tagging the item. The material may include at least N unique pieces of DNA, representing N digits of a bar code that identifies an attribute of the item. Each of the at least N pieces of DNA represents one value of a corresponding one of the N digits, N being a positive integer greater than 1. As described above, two different pieces of DNA may be used to represent two different bit values of the same digit of a binary number. In this embodiment, 2N unique pieces of DNA are used to represent an N digit binary number, and the tagging material will include 2N unique pieces of DNA. In FIG. 4, N is of the value 8. Alternatively, a single piece of DNA may be used to represent a given bit value such as 1 of a digit of a binary number, where the absence of such piece of DNA indicates a different bit value such as 0. In this embodiment, N unique pieces of DNA are used to represent a N digit binary number, and the tagging material will include N unique pieces of DNA. The unique DNA pieces may contain different DNA sequences or different lengths of DNA.

Using the above system, an attribute of an item can be identified. A material is provided for tagging the item, the material including at least N unique pieces of DNA, representing N digits of a bar code that identifies an attribute of the item, N being a positive integer greater than 1. Each of the at least N pieces of DNA represents one value of a corresponding one of the N digits. In this embodiment, the DNA pieces comprise tags that are not for identifying or authenticating the item itself. As described above, the DNA pieces may comprise tags for identifying attributes, such as origin or source of food, and/or other characteristics of the item, such as the attributes illustrated in FIGS. 1, 2, 3A and 3B. Of course, DNA pieces that identify or authenticate the item itself can also be included in the tagging material, where such DNA pieces will be different from the above described DNA pieces that are not used to identify the item itself. The technique described above in reference in FIG. 4 may be used for constructing DNA bar codes for identifying or authenticating the item itself, or for indicating attributes of the item that are not for identifying or authenticating the item itself.

Where an item has been tagged by the above described material that includes at least N unique pieces of DNA, representing N digits of a bar code that identifies one or more attributes of the item, the attribute or attributes may be determined by detecting the presence (or presence and absence) of pieces of DNA tagged to the item, and deriving a bar code from the detected pieces of DNA, such as by using the table in FIG. 4. The derived bar code is compared to the predetermined bar codes in the database or databases such as those described above in reference to FIGS. 1 and 2 to identify the food product origin or other food product attributes. As before, the attribute determined may not be the type that permits the item to be authenticated or identified, although the material can also include other DNA pieces that are used to identify the item itself.

The above technique of representation of the digits of a number is not limited to binary numbers, but may be used to represent numbers that are not binary. In such event, more than two unique pieces or segments of DNA may be assigned to represent the different values of the same digit.

Although the various aspects of the present invention have been described with respect to certain preferred embodiments, it is understood that the invention is entitled to protection within the full scope of the appended claims.

What is claimed is:

1. A method of applying a taggant to a material to identify an attribute of the material, comprising:
    selecting at least N unique independent pieces of DNA constructed to be distinguishable from the material, each unique independent piece of DNA corresponding to a binary digit of N binary digits of a DNA bar code that identifies the attribute of the material, N being a positive integer greater than one;
    mixing the selected at least N unique independent pieces of DNA to form a mixture containing the DNA bar code;
    mixing the mixture with a carrier to form the taggant; and applying the taggant to the material.

2. The method of claim 1, wherein the attribute identifies an origin of the material.

3. The method of claim 2, wherein the origin is further identified by an identification code on packaging of the material.

4. The method of claim 2, wherein the DNA bar code further identifies a second attribute which identifies a concentration of the material.

5. The method of claim 1, wherein applying the taggant comprises spraying the taggant onto the material.

6. The method of claim 1, wherein applying the taggant includes mixing the taggant with the material.

7. The method of claim 1, wherein the material is a food product.

8. The method of claim 1, wherein the carrier includes at least one of water, carnauba oil, silicone oil, sprout inhibitors, lipids, polysaccharides, proteins, vitamin C, and agar gel.

9. A method of tagging a material with a taggant comprising a DNA barcode, the DNA bar code comprising at least N unique independent pieces of DNA constructed to be distinguishable from the material, each unique independent piece of DNA corresponding to a binary digit of N binary digits of a DNA bar code that identifies the attribute of the material, N being a positive integer greater than one, the method comprising:
    for each unique independent piece of DNA of the at least N unique independent pieces of DNA, determining the corresponding binary digit of the N binary digits of the DNA bar code by:
        (1) causing a polymerase chain reaction of the unique independent piece of DNA through one or more heating cycles to increase a number of copies of the unique independent piece of DNA; and
        (2) detecting the number of copies of the unique independent piece of DNA to determine a value of the corresponding binary digit of the N binary digits of the DNA bar code; and
    based on the N binary digits of the DNA code, determining an attribute of the material.

10. The method of claim 9, wherein the attribute identifies an origin of the material.

11. The method of claim 10, wherein the origin is further identified by an identification code on packaging of the material.

12. The method of claim 10, wherein the DNA bar code further identifies a second attribute which identifies a concentration of the material.

13. The method of claim 9, wherein the material is tagged with the taggant by spraying the taggant onto the material.

14. The method of claim 9, wherein the material is tagged with the taggant by mixing the taggant with the material.

15. The method of claim 9, wherein the taggant further comprises a carrier and wherein the carrier comprises at least one of water, Carnauba oil, silicone oil, sprout inhibitors, lipids, polysaccharides, proteins, vitamin C, and agar gel.

16. A taggant applied to a material, the taggant comprising at least one DNA bar code for identifying an origin of the material, wherein the at least one DNA bar code includes at least N unique independent pieces of DNA, representing N digits of a bar code that identifies an attribute of the material, wherein each of the at least N unique independent pieces of DNA represents one value of a corresponding one of the N digits, N being a positive integer greater than one, and wherein each of the at least N unique independent pieces of DNA are constructed to be distinguishable from DNA present in the material.

17. The taggant of claim 16, wherein the attribute identifies an origin of the material.

18. The taggant of claim 17, wherein the origin is further identified by an identification code on packaging of the material.

19. The taggant of claim 16, wherein the taggant is applied to the material by spraying the taggant onto the material.

20. The taggant of claim 16 further comprising a carrier that includes at least one of water, Carnauba oil, silicone oil, sprout inhibitors, lipids, polysaccharides, proteins, vitamin C, and agar gel.

* * * * *